(12) United States Patent
Friedrichs et al.

(10) Patent No.: US 9,379,643 B2
(45) Date of Patent: Jun. 28, 2016

(54) ELECTROSURGICAL GENERATOR CONTROLLER FOR REGULATION OF ELECTROSURGICAL GENERATOR OUTPUT POWER

(75) Inventors: Daniel Friedrichs, Aurora, CO (US); Robert Erickson, Boulder, CO (US); James Gilbert, Boulder, CO (US)

(73) Assignees: The Regents of the University of Colorado, a body corporate, Denver, CO (US); Covidien LP, Boulder, CO (US)

( * ) Notice: Subject to any disclaimer, the term of this patent is extended or adjusted under 35 U.S.C. 154(b) by 977 days.

(21) Appl. No.: 13/334,041

(22) Filed: Dec. 21, 2011

(65) Prior Publication Data

US 2012/0215216 A1    Aug. 23, 2012

Related U.S. Application Data

(60) Provisional application No. 61/426,985, filed on Dec. 23, 2010, provisional application No. 61/530,528, filed on Sep. 2, 2011.

(51) Int. Cl.
*A61B 18/00* (2006.01)
*H02M 7/5387* (2007.01)
(Continued)

(52) U.S. Cl.
CPC ....... *H02M 7/53871* (2013.01); *A61B 18/1206* (2013.01); *A61B 2018/00678* (2013.01);
(Continued)

(58) Field of Classification Search
CPC ............... H02M 7/53871; A61B 2018/00726; A61B 2018/00827; A61B 18/1206; A61B 2018/00779; A61B 2018/00892; A61B 2018/00678
USPC .......................................................... 606/38
See application file for complete search history.

(56) References Cited

U.S. PATENT DOCUMENTS

| 6,979,987 B2 | 12/2005 | Kernahan et al. |
| 2005/0004564 A1* | 1/2005 | Wham et al. ............ 606/34 |

(Continued)

FOREIGN PATENT DOCUMENTS

| GB | 2164473 | 3/1986 |
| JP | 1127957 | 1/1999 |

(Continued)

OTHER PUBLICATIONS

Maxim Integrated, "MAX 5073 Dual-Output Buck or Boost Converter with Internal Power MOSFETs", https://datasheets.maximintegrated.com/en/ds/MAX5073.pdfcaptured Jan. 11, 2005.*

(Continued)

*Primary Examiner* — Carl H Layno
*Assistant Examiner* — Erin M Piateski
(74) *Attorney, Agent, or Firm* — Snell & Wilmer L.L.P.

(57) ABSTRACT

An electrosurgical generator may reduce unintended tissue damage by improving regulation of output power. The electrosurgical generator may control the power during a cycle, and react to a change in power if arcing occurs. Voltage sources, especially, demonstrate the tendency to have large, uncontrolled power excursions during normal electrosurgical use. The magnitude of the power excursions may be dependent on various factors. An exemplary electrosurgical generator control scheme reduces or minimizes the thermal spread by accurately supplying the specified power within a few cycles. Additionally, fast and accurate regulation provided by the constant voltage mode reduces or minimizes unintentional tissue charring. Thus, reduced thermal spread and charring should result in better surgical outcomes by reducing scarring and decreasing healing times. An electrosurgical generator controller may be configured to control both a DC-DC buck converter and a DC-AC boost inverter based in part on electrical parameters of the electrosurgical generator.

20 Claims, 9 Drawing Sheets

(51) Int. Cl.
*A61B 18/12* (2006.01)
*H02M 1/00* (2006.01)

(52) U.S. Cl.
CPC .............. *A61B2018/00726* (2013.01); *A61B 2018/00779* (2013.01); *A61B 2018/00827* (2013.01); *A61B 2018/00892* (2013.01); *H02M 2001/007* (2013.01)

(56) References Cited

U.S. PATENT DOCUMENTS

| | | | |
|---|---|---|---|
| 2005/0143725 A1 | 6/2005 | Daners | |
| 2007/0176584 A1* | 8/2007 | Chen | 323/282 |

FOREIGN PATENT DOCUMENTS

| | | |
|---|---|---|
| JP | 2006525096 | 11/2006 |
| JP | 2009500998 | 1/2009 |
| JP | 201011602 | 1/2010 |
| WO | 93/03679 | 3/1993 |
| WO | 2009081561 A1 | 7/2009 |
| WO | 2010025807 A1 | 3/2010 |

OTHER PUBLICATIONS

Google Archive search, demonstrating search result for MAX 5073 data sheet online on Jan. 11, 2005.*
IP Australia; Patent Examination Report mailed Aug, 2, 2013 in corresponding Australian App. No. 2011265566.
Partial European Search Report dated Oct. 14, 2014 for EP App. No. 11195600.9.
Zhang Kai et al: "Deadbeat control of PWM inverter with repetitive disturbance prediction"; Applied Power Electronics Conference and Exposition, 1999, APEC '99. Fourteenth Annual Dallas, TX, USA, Mar. 14-18, 1999, Piscataway, NJ.
Examination Report dated Jan. 14, 2015 in Australian Application No. 2011265566.
Search Report dated Feb. 5, 2015 in European Application No. 11195600.9.
Notice of Acceptance dated Apr. 22, 2015 in Australian Application No. 2011265566.
Office Action dated Jan. 27, 2016 in Japanese Application No. 2011-281839.
Extended European Search Report dated Apr. 21, 2016 in European Application No. 16151586.1.

* cited by examiner

CPM-controlled buck converter

ELECTROSURGICAL GENERATOR CONTROLLER FOR REGULATION OF ELECTROSURGICAL GENERATOR OUTPUT POWER

CROSS-REFERENCE TO RELATED APPLICATIONS

This application is a non-provisional of U.S. Provisional Application No. 61/426,985, entitled "DUAL CURRENT-MODE CONTROLLER FOR REGULATION OF ELECTROSURGICAL GENERATOR OUTPUT POWER," which was filed on Dec. 23, 2010. This application is also a non-provisional of U.S. Provisional Application No. 61/530,528, entitled "CONSTANT POWER SOURCE BY NONLINEAR CARRIER-CONTROL OF A BUCK CONVERTER FOR USE IN AN ELECTROSURGICAL GENERATOR," which was filed on Sep. 2, 2011. All of the contents of the previously identified applications are hereby incorporated by reference for any purpose in their entirety.

BACKGROUND OF THE INVENTION

An electrosurgical generator is commonly used in surgical practice to perform arc cutting and coagulation. The electrosurgical generator produces a high-frequency electric current to cut tissue with limited blood loss and enhanced cutting control compared to a metal blade. Standard industry practice is for electrosurgical generators to measure and average the alternating current (AC) output power over several cycles and use a low-bandwidth control loop to adjust the duty cycle of a pulse width modulated (PWM) converter, modulating the carrier of a fixed-output-impedance resonant inverter to achieve the desired output characteristic. However, the feedback control loop and several cycles average gives rise to latency issues.

One example of an industry practice is for electrosurgical generators to mimic medium-frequency (MF) amplitude modulated (AM) broadcast transmitters via a method commonly called the Kahn Envelope Elimination and Restoration technique. Such generators typically use a class-D or class-E RF output stage operating with constant voltage amplitude at the electrosurgical analogy of a carrier frequency. In various known embodiments, the generators are combined with an efficient converter power supply amplitude modulator, sometimes referred to as a class-S modulator. The converter power supply amplitude modulator may be configured to regulate the RF output voltage, current, or power dissipated in the tissue load to a desired power versus impedance characteristic called a power curve.

The assumption of such a technique is that the tissue load changes at rates substantially lower than the audio frequency (AF) band. However, this assumption is not entirely accurate when viewed through the prism of arcing, which is the primary mechanism of cutting and coagulation in electrosurgery. Arcing in electrosurgery can extinguish and re-ignite in the middle of a cycle, and changes in its characteristics can occur on scales much broader than the AF. Therefore, this assumption may be one of convenience more so than fact, since the feedback of RE for purposes of control is well known to be very difficult due to the lag introduced by most common feedback controller techniques.

The commonly used envelope feedback regulation for electrosurgery is accomplished by measuring and averaging the alternating current (AC) output power and load impedance via voltage and current sensor feedback over many (sometimes hundreds) of cycles. This approach is complex, and its slow response during arcing leads to poor regulation of the AC output power, resulting in undesirable thermal spread or other well known tissue damage such as charring and scarring. Thus, a need exists for an electrosurgical generator that overcomes these and other deficiencies.

SUMMARY OF THE INVENTION

Using a high frequency inverter to form an arc between the output of an electrosurgical generator and tissue of a patient, a surgeon can induce joule heating in the affected cells; this causes the desired surgical effects of cutting, coagulation, and dissection. In an exemplary embodiment, the electrosurgery utilizes joule heating produced by the electrosurgical generator. The electrosurgical generator produces an accurate power source output characteristic, to which maximum voltage and current limits are added. The voltage and current limits of the electrosurgical generator contribute to the safety of the process. Furthermore, in an exemplary embodiment the voltage and current limits are configured to produce particular tissue effects which may be desirable in various surgical applications.

In an exemplary embodiment, an electrosurgical generator control system produces constant power output without measuring output voltage or output current, and regulates the output power with substantially deadbeat control. The electrosurgical generator control system performs near deadbeat control by regulating inductor current to a specified value, equal to a reference current. Thus, in an exemplary embodiment, the electrosurgical generator control system achieves a desired inverter output characteristic with an efficient and substantially deadbeat control method for AC output power. Furthermore, an exemplary electrosurgical generator control system switches between operating modes based in part on at least one of a measured output voltage, a measured inductor current, and by observing a duty cycle command generated by the control system. Additionally, an exemplary control system provides the ability to adjust the voltage and current limits and facilitate precision control of desired tissue effects. The desired tissue effects may include at least one of cut depth and the amount of surface hemostatis versus thermal spread.

Compared to prior art electrosurgical generators, an exemplary electrosurgical generator reduces unintended tissue damage by improving regulation of output power. In accordance with an exemplary embodiment, an electrosurgical generator controls the power during a cycle, and reacts to a change in power if arcing occurs. Voltage sources, especially, demonstrate the tendency to have large, uncontrolled power excursions during normal electrosurgical use. The magnitude of the power excursions may be dependent on various factors. One factor is how far the surgeon is away from the tissue when an arc occurs in the sinusoidal cycle. Furthermore, in the prior art, the current sources may introduce long, unintended arcs, even if distance from the tissue was well controlled. Therefore, in an exemplary embodiment, the electrosurgical generator may be configured to control power within a carrier frequency cycle for full arc and plasma control throughout the cycle. Power control within the duration of a carrier frequency cycle is advantageous over the prior art systems because arcing occurs faster than typical voltage or current detection feedback mechanisms can respond.

Furthermore, the exemplary electrosurgical generator is less complex than prior art electrosurgical generators. Moreover, it is an objective of this application to present an inverter topology and control algorithm which combines current-mode and voltage-mode control to realize the desired output characteristic of an electrosurgical generator in a markedly simpler and more accurate fashion. By directing which of two conversion stages is to be current-mode controlled, constant power, constant current, and constant voltage outputs can be achieved with excellent regulation and fast transitions.

In an exemplary embodiment, effective regulation of an electrosurgical generator's output is important to achieving the desired clinical effects. If output power is allowed to exceed the desired value, excessive thermal spread may occur, unnecessarily damaging and scarring tissue and impeding healing. If maximum output voltage exceeds the limiting value, charring of tissue may occur, which is frequently undesirable as it may unnecessarily damage tissue and obscure the surgical field. Use of an exemplary electrosurgical generator control scheme in an electrosurgical generator can provide near-deadbeat regulation of output power. In addition, the electrosurgical generator control scheme tends to assure that thermal spread is minimized by accurately supplying the specified power within a few cycles. Additionally, in various embodiments, fast and accurate regulation provided by the constant voltage mode minimizes unintentional tissue charring. Thus, reduced thermal spread and charring should result in better surgical outcomes by reducing scarring and decreasing healing times.

BRIEF DESCRIPTION OF THE DRAWING FIGURES

A more complete understanding of the present invention may be derived by referring to the detailed description and draft statements when considered in connection with the appendix materials and drawing figures, wherein like reference numbers refer to similar elements throughout the drawing figures, and:

DETAILED DESCRIPTION

While exemplary embodiments are described herein in sufficient detail to enable those skilled in the art to practice the invention, it should be understood that other embodiments may be realized and that logical electrical and mechanical changes may be made without departing from the spirit and scope of the invention. Thus, the following detailed description is presented for purposes of illustration only.

In accordance with an exemplary embodiment, an electrosurgical generator controller operates with near-deadbeat control to maintain a desired AC output of an electrosurgical generator, which operates in at least one of a constant voltage mode, a constant current mode, and a constant power mode. The mode selection is generally based on the impedance associated with the tissue being cut. Different types of tissue, such as muscle and fat, have different impedances. In terms of electrosurgical operations, constant power output tends to uniformly vaporize tissue, resulting in clean dissection. Whereas constant voltage output tends to explosively vaporize or carbonize tissue ("black coagulation"), and constant current output tends to thermally coagulate tissue without vaporization ("White coagulation"). Carbonization is surgically useful if the surgeon wishes to rapidly destroy surface tissue, and thermal coagulation is regularly coupled with mechanical pressure to seal hepatic or lymphatic vessels shut. However, it is desirable for the surgeon to operate using constant power output and importantly, return to using constant power output as quickly as possible if there is deviation.

Figure 1:
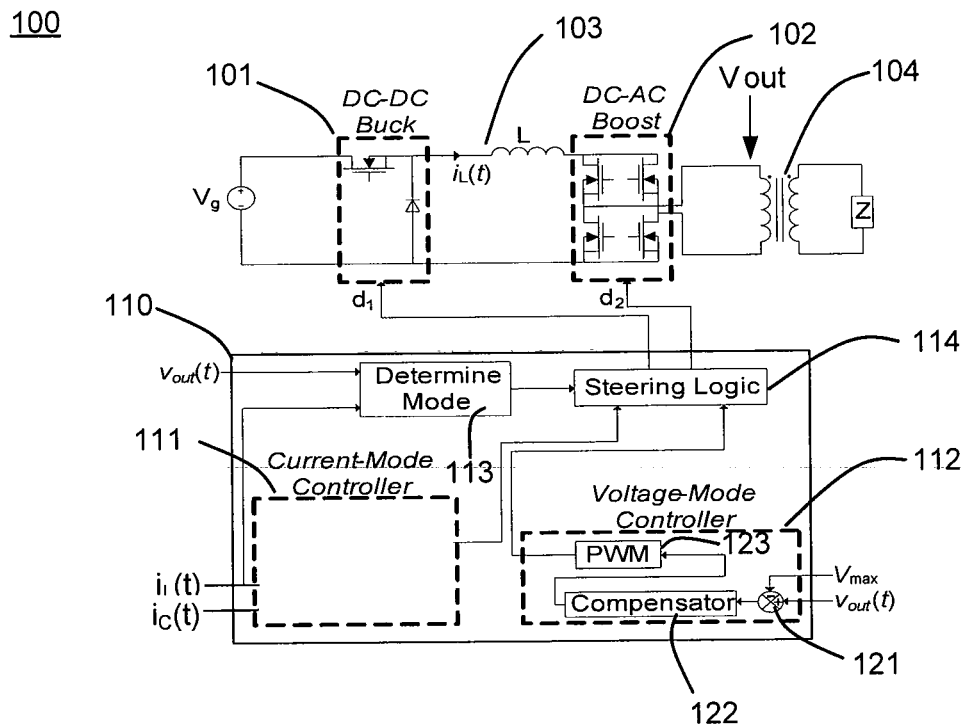
FIG. 1 illustrates a schematic of an electrosurgical generator circuit, in accordance with various embodiments.

With reference to the schematic shown in FIG. 1, in an exemplary embodiment, an electrosurgical generator 100 comprises a DC-DC buck converter 101, a DC-AC boost inverter 102, an inductor 103, a transformer 104, and an electrosurgical generator (ESG) control system 110. In the exemplary embodiment, a DC voltage source Vg is electrically coupled to DC-DC buck converter 101. Furthermore, inductor 103 is electrically coupled between DC-DC buck converter 101 and DC-AC boost inverter 102. The output of DC-AC boost inverter 102 transmits power to the primary winding of transformer 104, which passes through the secondary winding of transformer 104 to the load Z. Additionally, the load Z changes because tissue impedances vary, and also changes because the cutting process is an arc process. The impedance of an arc varies as it goes through several "phases" of formation and eventual extinguishment within a carrier frequency cycle.

In an exemplary embodiment, ESG control system 110 is in communication with both DC-DC buck converter 101 and DC-AC boost inverter 102. The ESG control system 110 is configured to control the duty cycle $d_1$ of DC-DC buck converter 101 and the duty cycle $d_2$ of DC-AC boost inverter 102. Additionally, ESG control system 110 is configured to measure power characteristics of electrosurgical generator 100, and control electrosurgical generator 100 based at least in part on the measured power characteristics. Examples of the measured power characteristics include the current through inductor 103 and the voltage at the output of DC-AC boost inverter 102. In various embodiments of control modes, ESG control system 110 controls buck converter 101 by generating duty cycles based on a combination and/or selection of duty cycle inputs from various controllers depending on the mode of operation (e.g., constant current, constant power, or constant voltage).

Figure 2:
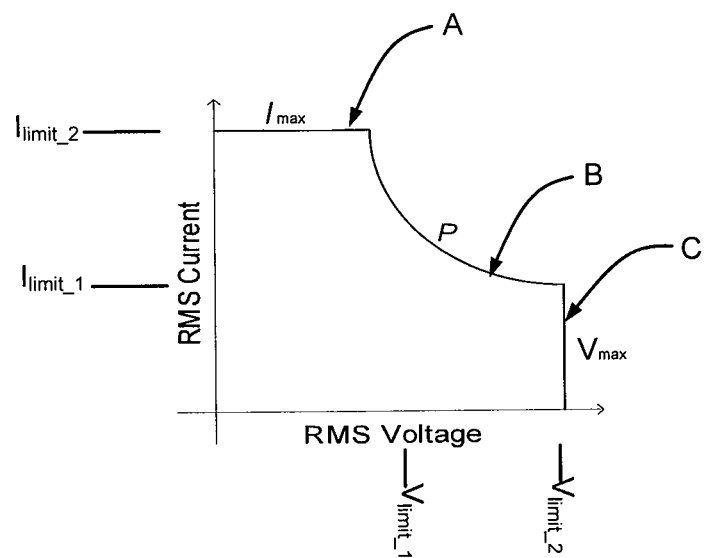
FIG. 2 illustrates a graphical representation of desired output characteristics, in accordance with various embodiments.

With respect to the AC output of the electrosurgical generator and in exemplary embodiments, "constant power" is defined to mean the average power delivered in each switching cycle is regulated to a substantially fixed value. Likewise, "constant voltage" and "constant current" are defined as the rms value of the AC voltage or current, respectively, being regulated to a substantially fixed value. In various embodiments, the substantially fixed values of the constant power, constant voltage, and constant current may be selected by a user or selected from a lookup table. In accordance with an exemplary embodiment, ESG control system 110 comprises a current-mode controller 111, a voltage-mode controller 112, a mode selector 113, and steering logic 114. In one exemplary embodiment, mode selector 113 compares the output voltage $v_{out}(t)$ and the inductor current $i_L(t)$ to "predetermined limits" (discussed in further detail herein) in order to determine the desired mode of operation of electrosurgical generator 100. An exemplary graphical representation of the desired output characteristics is illustrated in FIG. 2. In an exemplary embodiment, as the load impedance increases and causes the voltage to increase, the corresponding increasing output voltage triggers the transitioning of the operating mode from constant current (A) to constant power (B) to constant voltage (C). Similarly, in an exemplary embodiment, as the load impedance decreases and causes the current to increase, the corresponding decreasing output voltage triggers the opposite transitioning from constant voltage (C) to constant power (B) to constant current (A) operating modes.

Figure 3:
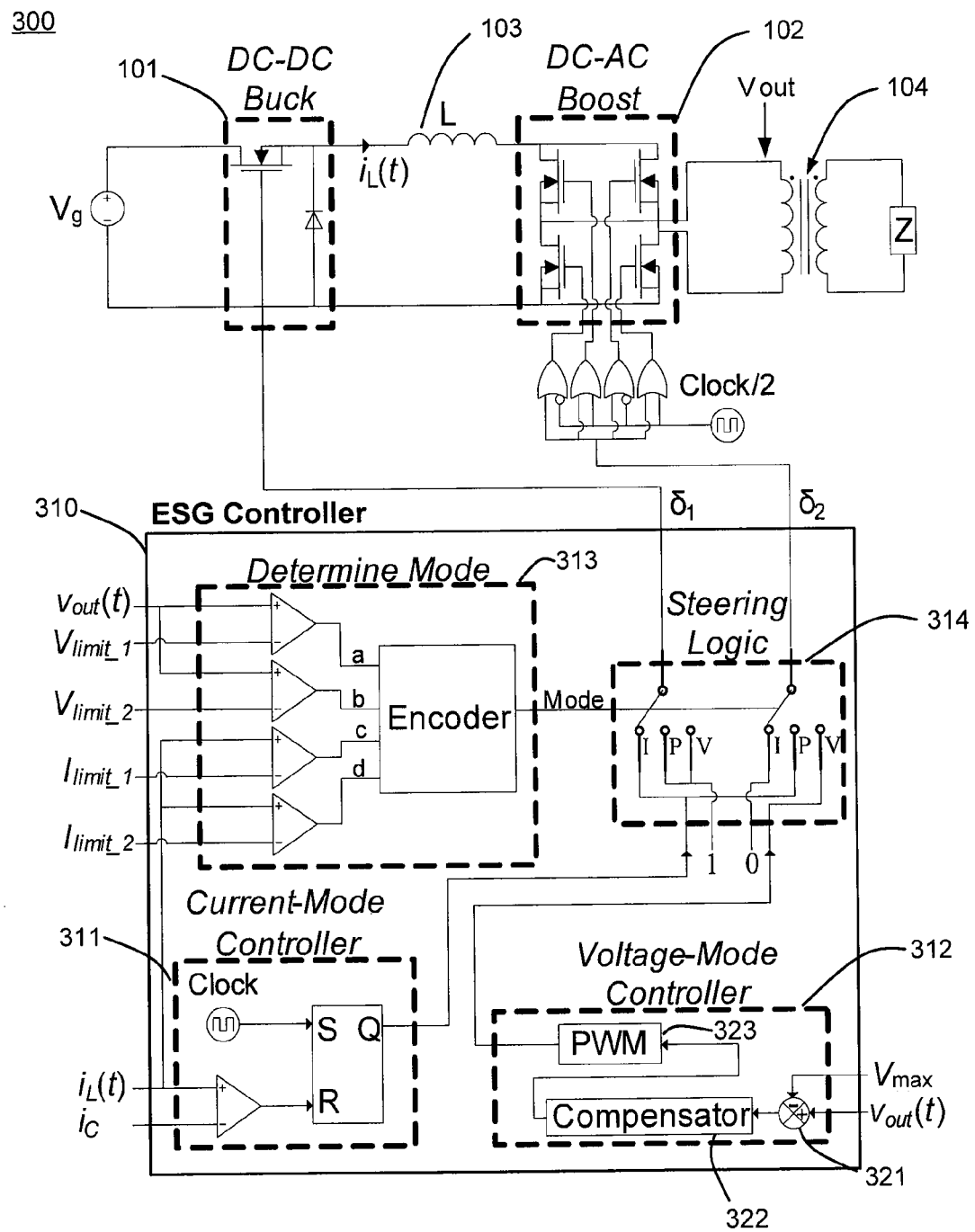
FIG. 3 illustrates a schematic of an electrosurgical generator circuit, in accordance with various embodiments.

In various embodiments, a constant power mode may be maintained by varying just the duty cycle of a DC-AC boost inverter. With reference to FIG. 3, an ESG control system 310 comprises a current-mode controller 311, a voltage-mode controller 312, a mode selector 313, and steering logic 314. In this exemplary embodiment, current-mode controller 311 compares the inductor current $i_L(t)$ to a control current limit $i_C$. In an exemplary embodiment, the control current limit $i_C$ is set by a user, or provided by a look-up table. In an exemplary embodiment, current-mode controller 311 uses a latch circuit to generate a switching waveform $\delta(t)$ with a duty cycle $d_1$. The inputs of the latch circuit are the current comparison and a clock signal. In an exemplary embodiment, the switching waveform $\delta(t)$ is switched "high" at the start of a switching period if the inductor current $i_L(t)$ is lower than control current limit $i_C$. Furthermore, in the exemplary embodiment, the switching waveform $\delta(t)$ is switched "low" in response to the inductor current $i_L(t)$ exceeding the control current limit $i_C$. In other words, a comparison of the inductor current $i_L(t)$ to control current limit $i_C$ facilitates adjusting the inductor current $i_L(t)$ to match the control current limit $i_C$. For small inductor current ripple, in other words $\Delta i_L \ll i_L$, the current-mode controller regulates the inductor current $i_L(t)$ to an approximately constant value, substantially equal to control current limit $i_C$.

In various embodiments and with continued reference to FIG. 3, voltage-mode controller 312 comprises a comparator 321, a compensator 322, and a pulse-width modulator 323. Furthermore, in various embodiments, voltage-mode controller 312 compares the output voltage $v_{out}(t)$ with a reference voltage $V_{max}$ at comparator 321. The output of comparator 321 is communicated to compensator 322 which in turn outputs an error signal that drives PWM 323. In the various embodiments, the output of compensator 322 is an input signal to PWM 323, which sets the duty cycle $d_2$ of the signal.

Furthermore, in various embodiments, mode selector 313 comprises an encoder and performs multiple comparisons. The output voltage $v_{out}(t)$ is compared with a first voltage limit $V_{limit\_1}$ to generate "signal a". The output voltage $v_{out}(t)$ is compared with a second voltage limit $V_{limit\_2}$ to generate "signal b". Similarly, the inductor current $i_L(t)$ is compared with a first current limit $I_{limit\_1}$ to generate a "signal c". The inductor current $i_L(t)$ is compared with a second current limit $I_{limit\_2}$ to generate a "signal d". In one exemplary embodiment and with reference to Table 1, the mode selection is set by mode selector 313 based on the above described comparisons. Table 1 lists comparison outcomes and corresponding mode. In an exemplary embodiment, Table 1 lists a "1" value if the output voltage or inductor current is greater than the compared limit, and a "0" value if the output voltage or inductor current is less than the compared limit. For example, if output voltage $v_{out}(t)$ exceeds both the first voltage limit $V_{limit\_1}$ and the second voltage limit $V_{limit\_2}$, then the encoder selects the constant voltage mode. Further, the second voltage limit $V_{limit\_2}$ is equivalent to reference voltage $V_{max}$, the same used in the comparison at voltage-mode controller 312.

TABLE 1

| a | b | c | d | Mode |
|---|---|---|---|------|
| 0 | 0 | 1 | 1 | I |
| 1 | 0 | 1 | 0 | P |
| 1 | 1 | 0 | 0 | V |

Constant Power Output

Figure 4:
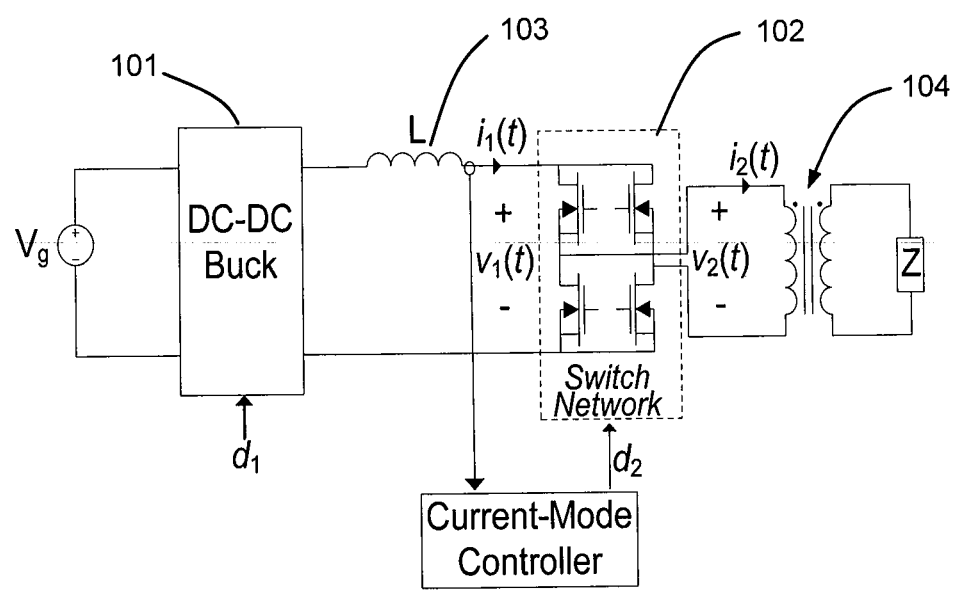
FIG. 4 illustrates a schematic of an exemplary electrosurgical generator in constant power output mode, in accordance with various embodiments.

In various embodiments, constant AC power output is achieved by setting duty cycle $d_1$ to a fixed value, and running the DC-AC boost inverter stage as a current-programmed boost inverter by varying duty cycle $d_2$. As previously mentioned, electrosurgical generator controller 310 performs near deadbeat control by regulating inductor current to an approximately constant value, equal to a control current limit $i_C$. For illustration purposes, FIG. 4 represents an exemplary schematic of the electrosurgical generator in constant power output mode.

In steady-state, the average voltage of $v_1(t)$ is constant in response to the input voltage Vg being constant, the DC-DC buck converter being bypassed by being set to 100% duty cycle, and no average voltage being able to exist across inductor L. The use of current programmed mode control results in the average current of $i_1(t)$ being regulated to an approximately fixed value with deadbeat or near-deadbeat control. In order to regulate $i_1(t)$, duty cycle $d_2$ is varied by the current mode controller to maintain $i_1(t)$ at a fixed value. Given the fixed voltage $v_1$ and current $i_1$, the power at input of DC-AC boost circuit 102 (i.e., a switch network) is also constant. In an exemplary embodiment, the switch network is nearly lossless, resulting in the output power being approximately equal to the input power. Since the input power is constant, the output power of DC-AC boost circuit 102 is also constant.

Constant Voltage Output

In various embodiments and with renewed reference to FIG. 3, constant voltage output is achieved by setting duty cycle $d_1$ of DC-DC buck converter 101 to a fixed value, and using voltage-mode control for duty cycle $d_2$ of DC-AC boost circuit 102. In an exemplary embodiment, the voltage-mode control involves measuring the output voltage $v_{out}(t)$ of DC-AC boost circuit 102 with a sensor network, feeding the sensed output voltage $v_{out}(t)$ to a control loop in voltage-mode controller 312, and adjusting the converter's duty cycle command based on the relative difference between the measured output voltage $v_{out}(t)$ and the reference output voltage $V_{max}$. In other words, the duty cycle $d_2$ is set to increase or decrease the output voltage to match $V_{max}$. In an exemplary embodiment, $V_{max}$ may be set by a user or based on values in a look-up table.

Constant Current Output

In an exemplary embodiment, constant current output is achieved by operating DC-AC boost circuit 102 at a fixed duty cycle $d_2$ and current-mode controlling DC-DC buck converter 101. In an exemplary embodiment, the current-mode control accurately controls the average inductor current such that the output of buck converter 101 is a constant current. In one embodiment, current-mode controller 111 compares inductor current $i_L(t)$ to control current limit $i_C$, where the control current limit $i_C$ is a desired fixed value. In other words, electrosurgical generator controller 310 is configured to vary duty cycle $d_1$ in order to maintain inductor current $i_L(t)$ at the fixed value. In various exemplary embodiments, as with $v_{out}(t)$, $i_L(t)$ is measured with a sensor and not an estimated value. As a result, the constant current output mode produces an AC output current whose magnitude is regulated with near-deadbeat speed.

Mode Transition Via Direct Measurement

In various embodiments, an electrosurgical generator system implementing the three modes of constant power, constant voltage, or constant current produces a very fast, very accurate regulation of the AC output characteristic. Various modes are impacted by measured characteristics, while other modes do not need to respond to the same measured characteristics. Specifically, electrosurgical generator controller 310 may switch between operating modes based in part on measured output voltage $v_{out}(t)$. Furthermore, electrosurgical generator controller 310 may adjust the operating parameters in the constant voltage mode based on the measured output voltage $v_{out}(t)$. In other words, the selection of which stage of the converter to current-mode control may be achieved with minimal feedback and without a need for extraneous measurements, averaging, or feedback of the output.

Transitioning between the three modes, in an exemplary embodiment, is determined by monitoring the voltage of the primary winding of transformer 104 and the inductor current. As previously described, in accordance with one exemplary embodiment, the transition from one mode to the next is summarized in Table 1. An exemplary ESG transitions modes from constant current to constant power to constant voltage as the output voltage $v_{out}(t)$ increases. Specifically, in an exemplary embodiment, electrosurgical generator 300 operates in the constant current mode if the output voltage $v_{out}(t)$ is less than a first voltage limit $V_{limit\_1}$. If the output voltage $v_{out}(t)$ exceeds the first voltage limit, electrosurgical generator 300 transitions to the constant power mode. If the output voltage $v_{out}(t)$ exceeds a second voltage limit $V_{limit\_2}$, electrosurgical generator 300 transitions to the constant voltage mode, where the output voltage $v_{out}(t)$ is limited and held constant. In an exemplary embodiment, the first voltage limit $V_{limit\_1}$ and the second voltage limit $V_{limit\_2}$ are set by a user or from a look-up table.

Similarly, electrosurgical generator 300 transitions from constant voltage mode to constant power mode to constant current mode as inductor current $i_L(t)$ increases. Specifically, in an exemplary embodiment, electrosurgical generator 300 operates in the constant voltage mode if the inductor current $i_L(t)$ does not exceed a first current $I_{limit\_1}$. If the inductor current $i_L(t)$ does exceed the first current $I_{limit\_1}$, then the mode transitions to the constant power mode. If the inductor current $i_L(t)$ exceeds a second current limit $I_{limit\_2}$, electrosurgical generator 300 transitions to the constant current mode, where the inductor current $i_L(t)$ is limited and held constant. In an exemplary embodiment, the first current limit $I_{limit\_1}$ and the second current limit $I_{limit\_2}$ are set by a user or from a look-up table.

ESG with Buck Converter and Boost Inverter Control

Figure 5:
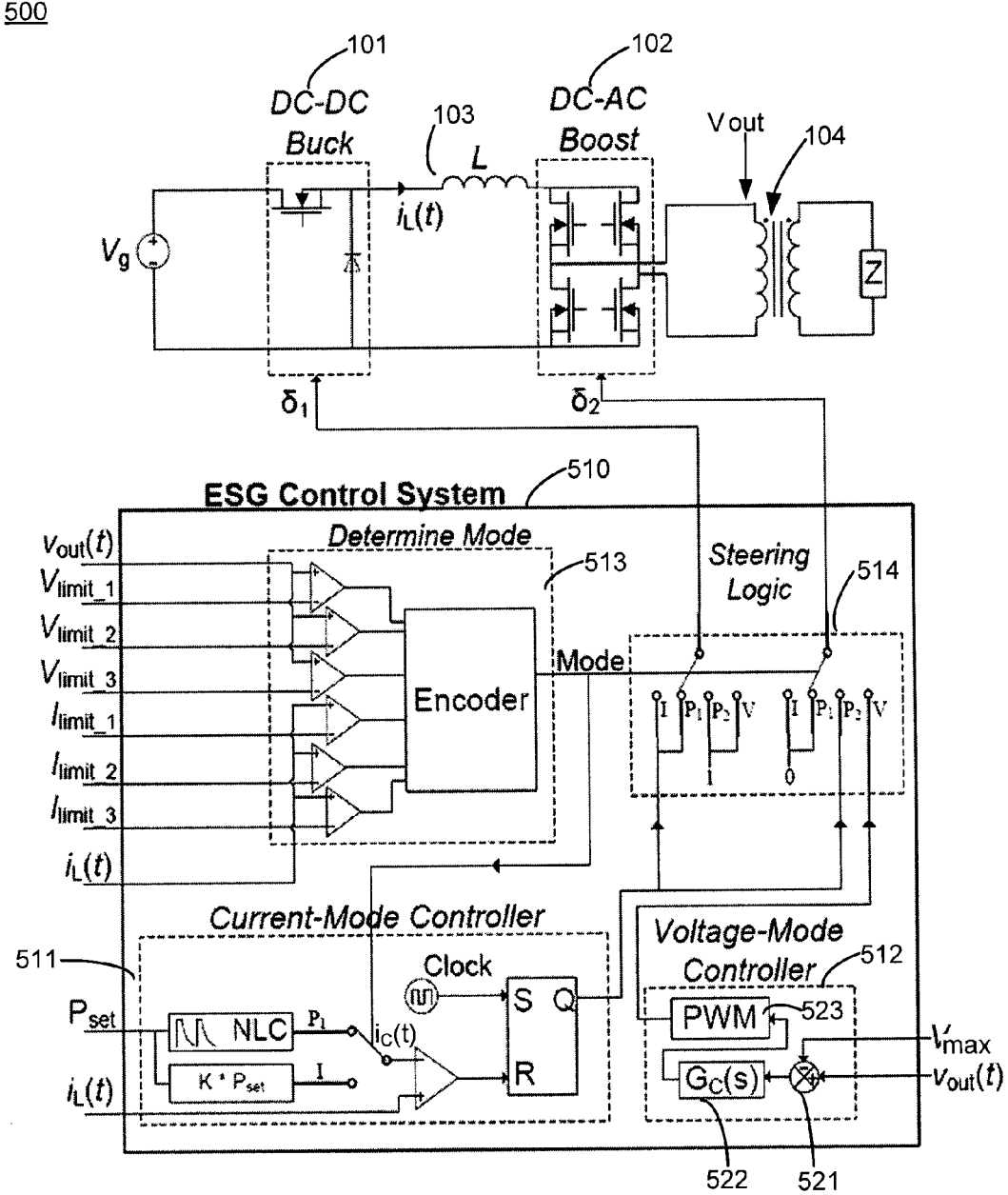
FIG. 5 illustrates a schematic of an exemplary electrosurgical generator circuit with buck converter and boost inverter control, in accordance with various embodiments.

In accordance with various embodiments and with reference to FIG. 5, an electrosurgical generator 500 having an ESG control system 510 comprises a current-mode controller 511, a voltage-mode controller 512, a mode selector 513, and steering logic 514. In various embodiments, the operational mode of electrosurgical generator 500 is one of constant (or maximum) current $I_{max}$, constant power $P_1$ from a buck converter, constant power $P_2$ from boost inverter, or constant (or maximum) voltage $V_{max}$. These modes are illustrated in an exemplary embodiment with reference to FIG. 6. The output selection of mode selector 513 is communicated to steering logic 514. In an exemplary embodiment, steering logic 514 controls which of at least one of current-mode controller 511 and voltage-mode controller 512 are enabled. Furthermore, steering logic 514 may select which conversion stage receives the output of current-mode controller 511 and/or voltage-mode controller 512, in various embodiments, steering logic 514 switches between operating either DC-DC buck converter 101 or DC-AC boost inverter 102 with current-mode control for constant power, depending on which portion of constant power regions ($P_1$ or $P_2$) is currently the operating mode. For example, the voltage mode controller 512 and/or current mode controller 511 may adjust the duty cycles $d_1$ and/or $d_2$ for the operating mode (constant current mode, constant voltage mode, constant power $P_1$, or constant power $P_2$). Furthermore, steering logic 514 selects the duty cycle that each of DC-DC buck converter 101 and/or DC-AC boost inverter 102 receives.

In various embodiments, the current-mode controller 511 compares the inductor current $i_L(t)$ to a nonlinear carrier control current limit $i_C(t)$. In an exemplary embodiment, the nonlinear carrier control current limit $i_C(t)$ is set by the selection of Pset, which may be done by a user, or provided by a look-up table. In an exemplary embodiment, current-mode controller 511 uses a latch circuit to compare inductor current $i_L(t)$ to control current limit $i_C(t)$, comprising either a current limit signal (I) or a power limit signal ($P_1$). The control signal for a P/I switch is the mode signal, which is communicated from mode selector 513. The inputs of the latch circuit are a clock signal and the comparison of control current limit $i_C(t)$ and inductor current $i_L(t)$, comprising one of the current limit signal (I) or a power limit signal ($P_1$). The selection of the current-mode controller 511 output is in response to the current mode of the electrosurgical generator 500. The operating mode of the electrosurgical generator 500 may be communicated from the output of mode selector 513. In an exemplary embodiment, the switching waveform $\delta(t)$ is switched "high" at the start of a switching period if the inductor current $i_L(t)$ is lower than nonlinear carrier control current limit $i_C(t)$. Furthermore, in the exemplary embodiment, the switching waveform $\delta(t)$ is switched "low" in response to the inductor current $i_L(t)$ exceeding the nonlinear carrier control current limit $i_C(t)$. In other words, a comparison of the inductor current $i_L(t)$ to nonlinear carrier control current limit $i_C(t)$ facilitates adjusting pulse duration of buck converter's 101 duty cycle, as previously described.

To generate and control a constant current from electrosurgical generator 500, the average value of inductor current $i_L(t)$ is controlled to be substantially equal to fixed control current limit K*Pset, which is a fixed, non-time varying value. For small inductor current ripple, in other words $\Delta i_L \ll i_L$, the current-mode controller regulates the inductor current $i_L(t)$ to an approximately constant value, substantially equal to the fixed control current limit.

Figure 7:
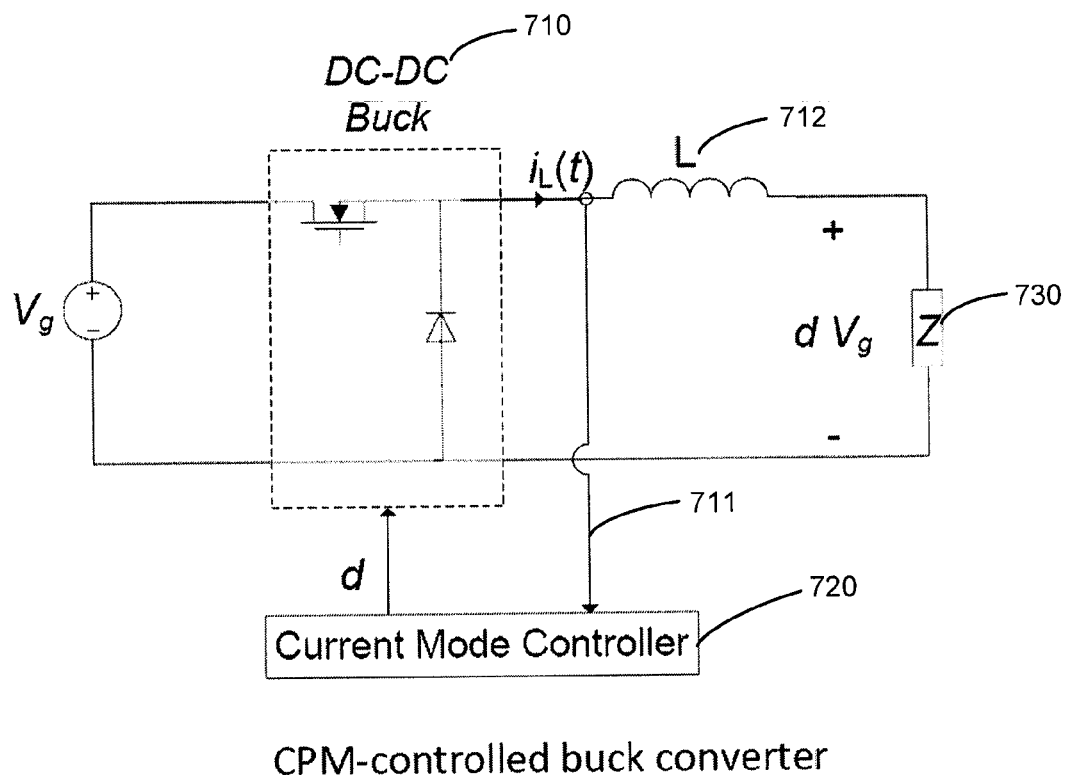
FIG. 7 illustrates a schematic of an exemplary buck converter circuit with current programmed mode control, in accordance with various embodiments.

With respect to using a buck converter to generate substantially constant power (e.g., constant power $P_1$), implementation of a nonlinear carrier control current limit is further described. In addition to generating a constant power source based on varying just the duty cycle of a DC-AC boost inverter, a buck converter may also be configured to generate substantially constant power output. In accordance with various exemplary embodiments, substantially constant power output of a buck converter may be achieved by adjusting a duty cycle's active period for the buck converter, in an exemplary embodiment and with reference to FIG. 7, a buck converter system comprises a power source Vg, a buck converter circuit 710, a controller 720, and a load 730. The impedance of the load may be static or dynamic. In the various embodiments, the controller 720 receives a feedback signal 711 representative of the output of the buck converter 710. In an exemplary embodiment, the feedback signal 711 is a measurement of the current passing through an inductor 712 coupled to buck converter circuit 710.

In various embodiments, controller 720 receives real time feedback of the inductor current $i_L(t)$ from the buck converter. The feedback signal 711 is used by controller 720 to adjust the duration of the active and non-active portions of the duty cycle. Adjustment of the duty cycle portions in real time, or substantially in real time, may be configured to produce a constant power source from buck converter 710. In various embodiments, two characteristics of the inductor feedback signal 711 are used to make the determination of duty cycle adjustments. The two characteristics are, first, the value of inductor current $i_L(t)$ and second, the slope of the change in the inductor current $i_L(t)$. These two characteristics may be used to provide implied information regarding the current and voltage of the output power into load 730, and this implied information may be used to adjust the magnitude of the duty cycle in real time and produce substantially constant power output.

The pulse duration of the duty cycle of DC-DC buck converter 710 is varied using current mode controller 720. The varying pulse duration of the duty cycle controls the inductor current $i_L(t)$, which is responsive to load 730 in contact with buck converter 710. As the impedance of load 730 varies, the voltage across inductor 712 also varies, and the current through inductor 712 varies as well.

Figure 8:
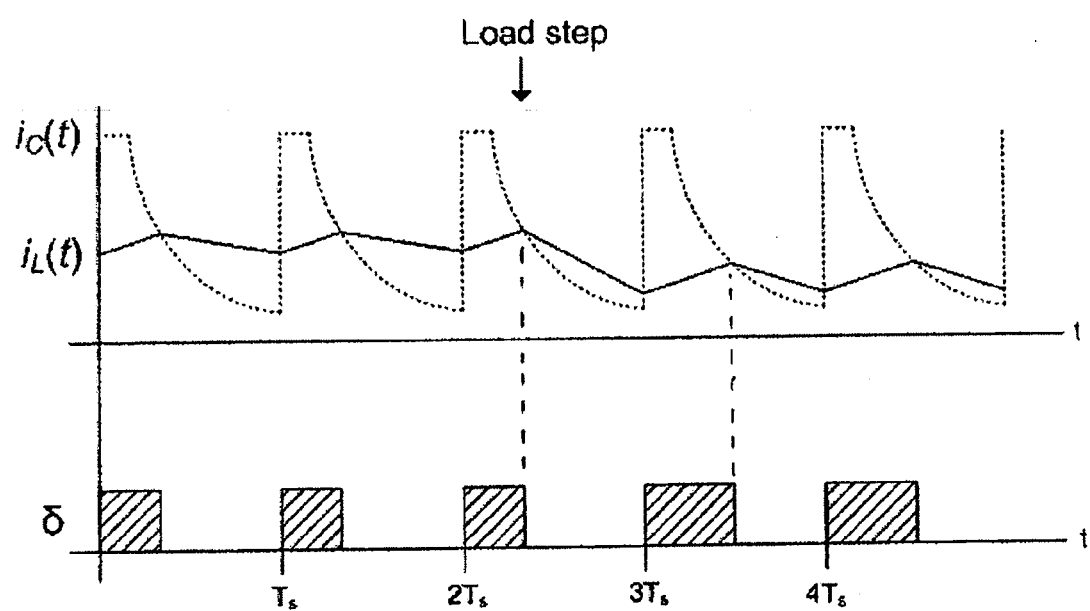
FIG. 8 illustrates a graphical representation of the interaction between the nonlinear carrier control current limit and measured inductor current, and the establishing of a corresponding duty cycle, in accordance with various embodiments.

Described in more detail, at the beginning of the buck converter duty cycle, the active portion (also referred to as the pulse duration of the pulse period or the "on" portion) of the duty cycle is initiated. With respect to a buck converter, the active portion of the pulse period closes a switch between a power source and an inductor, thereby allowing power to flow through the inductor. In various embodiments and with reference to FIG. 8, the inductor feedback signal $i_L(t)$ is compared to a nonlinear carrier control current $i_C(t)$. The nonlinear carrier control current $i_C(t)$ is a time-varying, nonlinear control signal that may be set for customized uses based on the desired output power. In response to the inductor feedback signal $i_L(t)$ exceeding the control current $i_C(t)$, the duty cycle switches to the non-active portion (also referred to as the "off" portion). The duty cycle stays in the non-active portion until the end of the pulse period. At the end of the pulse period, the cycle begins again with another pulse duration.

In various embodiments, the switching cycle has a fixed time period. Comparison of the inductor feedback signal $i_L(t)$ and the nonlinear carrier control current $i_C(t)$ is able to facilitate substantially constant power output based on a variable division of active and non-active portions of the duty cycle. As briefly described and with continued reference to FIG. 8, the inductor current value and the slope of the change in the inductor current $i_L(t)$ are used to adjust the duty cycle. By way of example and without limitation, the inductor current slope affects the timing of how long the inductor current $i_L(t)$ is less than the nonlinear carrier control current $i_C(t)$. A lower slope value indicates that the inductor current $i_L(t)$ is increasing at a slower rate, and therefore it will take a longer period of time until the inductor current $i_L(t)$ exceeds the control current $i_C(t)$. In other words, the more time is takes for the inductor current $i_L(t)$ to exceed the control current $i_C(t)$, the longer the corresponding pulse duration. For example, see the comparison between the pulse duration at 2 $T_S$ and 3 $T_S$. A higher slope value of inductor current $i_L(t)$ indicates that the inductor current is increasing at a quicker rate, and therefore it will take a shorter period of time until the inductor current $i_L(t)$ exceeds the control current limit $i_C(t)$. The shorter period of time results in the duty cycle staying in the active portion for a shorter period and having shorter pulse duration.

The nonlinear carrier control current $i_C(t)$ is part of a nonlinear carrier control (NLC) technique. In various embodiments, the NLC technique applied to the buck converter is based on a nonlinear time dependent variable, which is the nonlinear carrier. In various embodiments, the nonlinear time dependent variable is determined by the input voltage Vg, period of the switching cycle, and the desired power output. The application of NLC technique and production of substantially constant power output creates a buck converter that is a power source. In other words, the buck converter may implement NLC techniques to generate a fixed amount of power and be a power source. In contrast, prior art use of NLC techniques was typically configured to cause a converter to absorb a fixed amount of power and be a power sink. One of the benefits of using NIX control techniques is that a buck converter in combination with a boost inverter can produce a constant power source over a wider impedance range than using just a boost inverter alone. For example, an electrosurgical generator as described herein is capable of operating over an impedance range of about 64 to 4000 ohms. Using both a boost inverter and buck converter to source constant power facilitates operating over the wide impedance range without unreasonably high peak voltages.

In accordance with various exemplary methods, producing constant power output in a buck converter with a load having variable resistance includes turning on a switch of the buck converter at the beginning of the duty cycle to initiate a pulse, and monitoring the current through the inductor. The inductor current linearly increases while the buck converter is operating in the active portion of the duty cycle. The exemplary method may further include comparing, at a control circuit, the inductor current $i_L(t)$ to a nonlinear carrier control current $i_C(t)$, and turning off the switch of the buck converter in response to the magnitude of the inductor current meeting or exceeding the magnitude of the nonlinear carrier control current. In response to turning off the switch of the buck converter, the inductor current ramps down during the non-active portion of the duty cycle. The changing inductor current slope corresponds to the changing impedance of the load, which may be used to adjust the pulse duration of the duty cycle in order to produce substantially constant power output from the buck converter. In various embodiments, the nonlinear carrier control current is derived from the following equation:

$$i_C(t) = \frac{P}{Vg} * \frac{Ts}{t},$$

where P is power at the load, Ts is the switching cycle period, Vg is the input DC voltage source magnitude, and t is the time (assuming t=0 occurs at the start of the switching cycle). Additionally, as is understood by one in the art, the inductor current has minor fluctuation during each cycle due to turning the buck converter on and off, and the minor fluctuation may not be due to any change in the load impedance. In various embodiments, changes to the load impedance result in a change in inductor current slopes and a change to the average value of the inductor current.

Although a buck converter with substantially constant power output is described in terms of implemention in an electrosurgical generator, such a buck converter may also be implemented in various applications, such as are welding and gas-discharge lamps (i.e. street lamps).

In an exemplary embodiment and with renewed reference to FIG. 5, voltage-mode controller 512 comprises a comparator 521, a compensator 522, and a pulse-width modulator (PWM) 523. Furthermore, in an exemplary embodiment, voltage-mode controller 512 compares the measured output voltage $v_{out}(t)$ with a reference voltage $V_{max}$ at comparator 521. The output of comparator 521 is communicated to compensator 522 which in turn outputs an error signal that drives PWM 523. In the exemplary embodiment, the output of compensator 522 is an input signal to PWM 523, which sets the duty cycle $d_2$ of the signal in certain modes.

In various embodiments, constant voltage output may also be achieved by setting duty cycle $d_1$ of DC-DC buck converter 101 to a fixed value, and limiting the duty cycle $d_2$ of DC-AC boost inverter 102 to a maximum duty cycle $d_{max}$. Implementing a duty cycle limit on DC-AC boost inverter 102 during the constant voltage output generally amounts to running DC-AC boost inverter 102 in an open-loop. In various embodiments, limiting the duty cycle $d_2$ of DC-AC boost inverter 102 to a maximum duty cycle $d_{max}$ results in poorer steady-state output voltage regulation in comparison to mode transitions using direct measurement, but provides the significant advantage of limiting the peak output voltage on a per-cycle basis, with little or no risk of transient overshoot. For various electrosurgical applications, the steady-state value of the maximum output voltage $v_{out}(t)$ is of lesser importance, as it would be unusual to operate in this output mode for any length of time. Per-cycle transient voltage limiting, however, may be highly useful as a means to limit potential undesirable arcing. Additionally, in various embodiments, a maximum duty cycle may be easily varied without the need to linearize an output voltage measurement or tune a compensator, and in this exemplary embodiment no sensor is required on the output since no direct measurement is taken.

Figure 6:
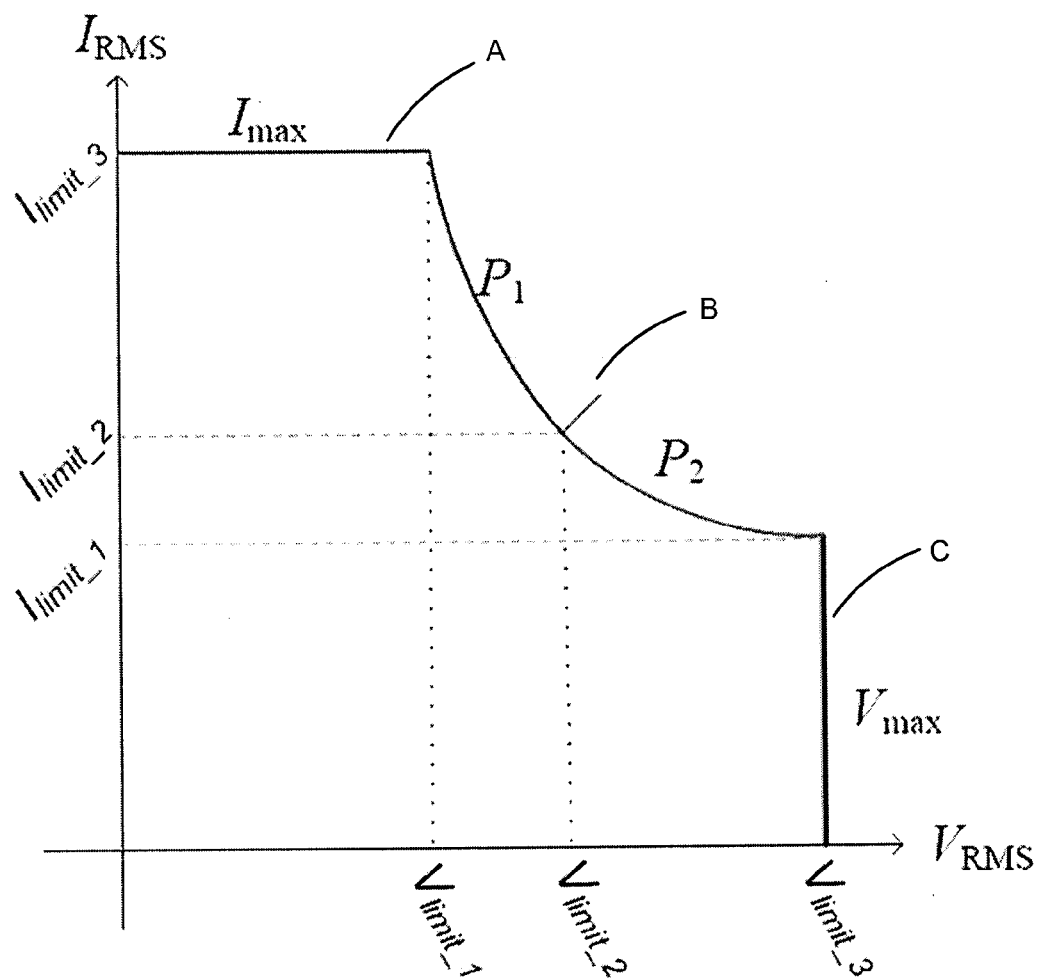
FIG. 6 illustrates another graphical representation of desired output characteristics, in accordance with various embodiments.

Furthermore, configurations such as exemplary electrosurgical generator 500 may have additional inputs into the mode selection. In another exemplary embodiment and with reference to FIG. 5, mode selector 513 comprises an encoder and performs multiple comparisons. The output voltage $v_{out}(t)$ is compared with three separate voltage limits ($V_{limit\_1}$, $V_{limit\_2}$, $V_{limit\_3}$) to generate three voltage comparison signals. Similarly, the inductor current $i_L(t)$ is compared with three separate current limits ($I_{limit\_1}$, $I_{limit\_2}$, $I_{limit\_3}$) to generate three current comparison signals. With reference to FIG. 6, in various embodiments, mode selector 513 uses the voltage comparison signals and the current comparison signals to determine whether electrosurgical generator 500 is operating in the constant current output region (A), the region $P_1$ of the constant power output region (B), the region $P_2$ of the constant power output region (B), or the constant voltage output region (C). Furthermore, the output mode signal from mode selector 513 controls the switch position in steering logic 514. Moreover, the output mode signal from mode selector 513 controls the switch position in current-mode controller 511. For example, if output voltage $V_{out}(t)$ exceeds the first voltage limit $V_{limit\_1}$, the second voltage limit $V_{limit\_2}$, and the third voltage limit $V_{limit\_3}$, then the encoder selects the constant voltage mode. The constant voltage mode signal from mode selector 513 would cause the switches' position of steering logic 514 to be "V". As another example, if output voltage $v_{out}(t)$ exceeds the first voltage limit $V_{limit\_1}$ but does not exceed the the second voltage limit $V_{limit\_2}$, and inductor current $i_L(t)$ exceeds first current limit $I_{limit\_1}$ and second current limit $I_{limit\_2}$, but does exceed $I_{limit\_3}$, then mode selector 513 determines that the operating mode is constant power $P_1$. The constant power $P_1$ mode signal from mode selector 513 would cause the switches' position of steering logic 514 to be "$P_1$" as illustrated in FIG. 5 and Table 2. The values "1" and "0" represent any fixed value between 0% and 100% that is not closed-loop controlled. In other words, there is no feedback signal actively changing the fixed values represented by "1" and "0".

TABLE 2

Duty cycle of buck and boost conversion stages by operating mode

| | Constant Current $I_{max}$ | Constant Power $P_1$ | Constant Power $P_2$ | Constant Voltage $V_{max}$ |
|---|---|---|---|---|
| Buck Converter | ESG controlled with fixed control current limit | ESG controlled with nonlinear carrier control current limit | 1 | 1 |
| Boost Inverter | 0 | 0 | ESG controlled with fixed control current limit | Voltage mode controlled |

Constant Power Output

In an exemplary embodiment, constant AC power output is achieved by setting one or both of duty cycle $\delta_1$ and duty cycle $\delta_2$ to desired values. Moreover, electrosurgical generator 500 operates with constant AC power output in either a first constant power region $P_1$ or a second constant power region $P_2$. In various embodiments, the converter switches between generating constant power using boost inverter 102 or buck converter 101, depending on the impedance of the load. Moreover, in various embodiments, electrosurgical generator 100 may operate both boost inverter 102 and buck converter 101 at the same time, which results in a constant power output having a high voltage and low power.

In steady-state and operating in first constant power region $P_1$, inductor current $i_L(t)$ is compared to a nonlinear carrier control current $i_C(t)$ in current-mode controller 511. The pulse duration of the duty cycle of the DC-DC buck converter is varied using the current mode controller 511. The varying pulse duration of the duty cycle controls the inductor current $i_L(t)$, which is responsive to the load in contact with the buck converter. As the impedance of the load varies, the voltage across the inductor $v_L(t)$ also varies, and the current through the inductor $i_L(t)$ varies as well. As previously described, at the beginning of the duty cycle, the active portion of the duty cycle is initiated. In response to the inductor current $i_L(t)$ exceeding the nonlinear carrier control current $i_C(t)$, the duty cycle switches to the non-active portion. The duty cycle stays in the non-active portion until the end of the duty cycle, upon which the next duty cycle begins in the active portion, in alternative embodiments, during the comparison of the inductor feedback signal $i_L(t)$ and the nonlinear carrier control current $i_C(t)$, once the control current exceeds the inductor current, the duty cycle switches to the active portion. In accordance with the exemplary embodiment, electrosurgical generator 500 generates constant power using buck converter 101 during first constant power region $P_1$.

In steady-state and operating in second constant power region $P_2$, the average voltage of $v_1(t)$ is constant in response to the input voltage Vg being constant, the DC-DC buck converter being bypassed by being set to 100% duty cycle, and no average voltage being able exist across inductor 103. The use of current programmed mode control results in the average current of $i_1(t)$ being regulated to an approximately fixed value with deadbeat or near-deadbeat control. In order to regulate $i_1(t)$, duty cycle $\delta_2$ is varied by the current mode controller to maintain $i_1(t)$ at a fixed value. Given the fixed voltage and current, the power at input of DC-AC boost inverter (i.e., a switch network) is also constant. In an exemplary embodiment, the switch network is nearly lossless, resulting in the output power being approximately equal to the input power. Since the input power is constant, the output power of DC-AC boost inverter 102 is also constant.

Constant Voltage Output

In an exemplary embodiment, constant voltage output is achieved by setting duty cycle $\delta_1$ of DC-DC buck converter 101 to a fixed value, and duty cycle $\delta_2$ of DC-AC boost inverter 102 is voltage-mode controlled. In an exemplary embodiment, the voltage-mode control involves measuring the output voltage $v_{out}(t)$ of DC-AC boost inverter 102 with a sensor, feeding the sensed output voltage to a control loop in voltage-mode controller 512, and adjusting the converter's duty cycle command based on the relative difference between the measured output voltage and the reference output voltage. In other words, the duty cycle $\delta_2$ is set to increase or decrease the output voltage to match $V_{max}$. In an exemplary embodiment, $V_{max}$ may be set by a user or based on values in a look-up table. In an alternative embodiment, the boost inverter is run at a fixed duty cycle with no feedback of the output voltage.

Constant Current Output

In an exemplary embodiment, constant current output is achieved by operating DC-AC boost inverter 102 at a fixed duty cycle $\delta_2$ and current-mode controlling DC-DC buck converter 101. In an exemplary embodiment, the current-mode control accurately controls the average inductor current such that the output of buck converter 101 is a constant current. In one constant current embodiment, current-mode controller 511 compares inductor current $i_L(t)$ to a control current limit $i_C(t)$. In various embodiments, control current limit $i_C(t)$ may be a selected, fixed value or may be set by K*Pset, where K*Pset is a constant current set by the user during use. In various embodiments, Pset is set during the design stage. In other words, ESG control system 510 is configured to vary duty cycle $\delta_1$ in order to maintain inductor current $i_L(t)$ at the fixed value. As a result, the constant current output mode produces an AC output current whose magnitude is regulated with near-deadbeat speed.

Electrosurgical Generator Modes

Similar to the transition of modes in electrosurgical generator 300, in an exemplary embodiment, electrosurgical generator 500 also implements the three modes of constant power, constant voltage, or constant current to produce a very fast, very accurate regulation of the AC output characteristic. Various modes are impacted by measured characteristics, while other modes do not need to respond to the same measured characteristics. Specifically, ESG control system 510 switches between operating modes based in part on measured characteristics, such as inductor current and voltage. In other words, the selection of which stage of the converter to current-mode control is achieved with minimal feedback and without a need for extraneous measurements, averaging, or feedback of the output. Also, and as previously mentioned, the ESG control system 510 performs near deadbeat control by regulating inductor current to an approximately constant value, equal to a reference current.

Mode Transition Via Direct Measurement

Transitioning between the three modes, in an exemplary embodiment, is determined by monitoring the voltage of the primary winding of transformer 104 and the inductor current. Furthermore, the determination of transitioning between the modes may also based on the voltage and current of the primary winding of transformer 104. In various embodiments, ESG control system 510 transitions modes from constant current to constant power to constant voltage as the output voltage $v_{out}(t)$ increases.

Specifically, in various embodiments, electrosurgical generator 500 operates in the constant current mode if the output voltage $v_{out}(t)$ is less than a first voltage limit ($V_{limit\_1}$). If the output voltage $v_{out}(t)$ exceeds the first voltage limit, electrosurgical generator 500 transitions to a first constant power mode ($P_1$). If the output voltage $v_{out}(t)$ exceeds a second voltage limit ($V_{limit\_2}$), electrosurgical generator 500 transitions to a second constant power mode ($P_2$). If the output voltage $v_{out}(t)$ exceeds a third voltage limit ($V_{limit\_3}$), electrosurgical generator 500 transitions to the constant voltage mode. Where the output voltage $v_{out}(t)$ is limited and held constant. In an exemplary embodiment, the first voltage limit ($V_{limit\_1}$), the second voltage limit ($V_{limit\_2}$), and the third voltage limit ($V_{limit\_3}$) are set by a user or from a look-up table.

Moreover, an exemplary ESG control system 510 transitions from constant voltage mode to constant power mode to constant current mode as inductor current $i_L(t)$ increases. Specifically, in an exemplary embodiment, electrosurgical generator 500 operates in the constant voltage mode if the inductor current $i_L(t)$ does not exceed a first current limit ($I_{limit\_1}$) if the inductor current $i_L(t)$ does exceed the first current limit ($I_{limit\_1}$), then the mode transitions to the second constant power mode ($P_2$). If the inductor current $i_L(t)$ exceeds a second current limit ($I_{limit\_2}$), then the mode transitions to the first constant power mode ($P_1$). If the inductor current $i_L(t)$ exceeds a third current limit ($I_{limit\_3}$), electrosurgical generator 500 transitions to the constant current mode, where the inductor current $i_L(t)$ is limited and held constant. In an exemplary embodiment, the first current limit ($I_{limit\_1}$), the second current limit ($I_{limit\_2}$), and the third current limit ($I_{limit\_3}$) are set by a user or from a look-up table.

Mode Transition Via Duty Cycle

In various alternative embodiments, the selection of operating modes may be based in part on the duty cycle. For example, if the electrosurgical generator is operating in constant power mode using the buck converter and the duty cycle reaches 100% active, the controller may be configured to switch to the constant power mode using the boost inverter. The switch to the boost inverter enables the electrosurgical generator to operate over a higher range of impedances.

Figure 9:
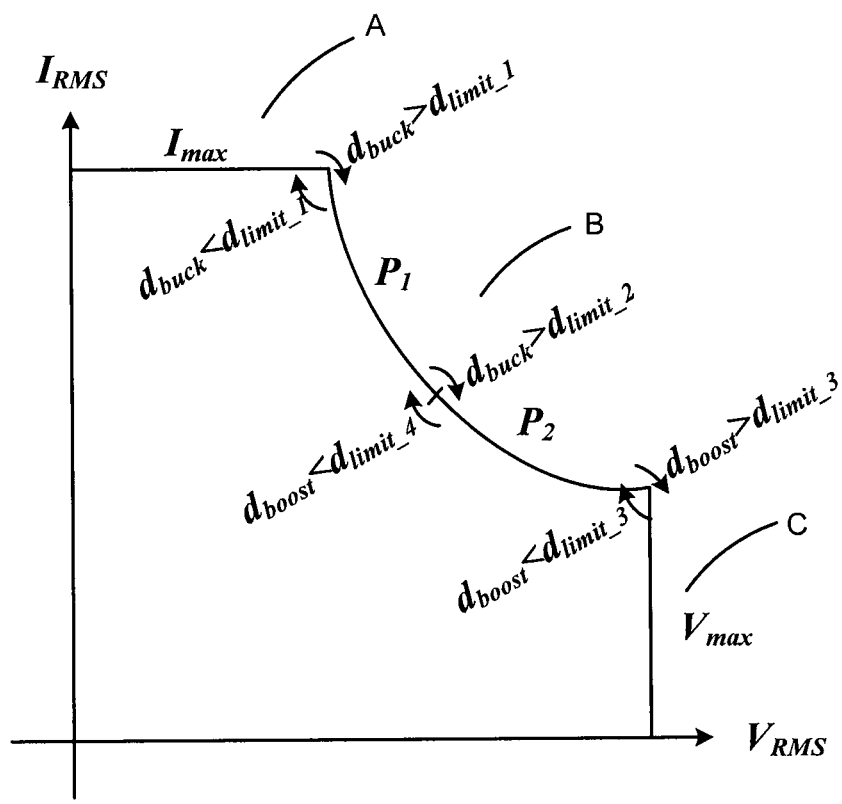
FIG. 9 illustrates yet another graphical representation of desired output characteristics using duty cycle limits, in accordance with various embodiments.

In various embodiments, duty cycle limits may be used in the electrosurgical generator controller to control the mode transitions. With reference to FIG. 9, in various embodiments, an exemplary mode selector may use duty cycle comparison signals to determine whether electrosurgical generator 500 is operating in the constant current output region (A), the region $P_1$ of the constant power output region (B), the region $P_2$ of the constant power output region (B), or the constant voltage output region (C).

In an exemplary embodiment, the duty cycle comparison signals are generated from the comparison of the buck converter duty cycle $d_{buck}$ (also referred to as $d_1$ herein) and the boost inverter duty cycle $d_{boost}$ (also referred to as $d_2$ herein) to at least four separate duty cycle limits ($d_{limit\_1}$, $d_{limit\_2}$, $d_{limit\_3}$, and $d_{limit\_4}$). For example, if the buck converter duty cycle $d_{buck}$ exceeds the first duty cycle limit $d_{limit\_1}$ and the second duty cycle limit $d_{limit\_2}$, and also the boost inverter duty cycle $d_{boost}$ exceeds the third duty cycle limit $d_{limit\_3}$, then the electrosurgical generator operates in the constant voltage mode and constant voltage output region (C). Similarly, if the boost inverter duty cycle $d_{boost}$ is less than the third duty cycle limit $d_{limit\_3}$, and the fourth duty cycle limit $d_{limit\_4}$, and the buck converter duty cycle $d_{buck}$ is less than the first duty cycle limit $d_{limit\_1}$, then the electrosurgical generator operates in the constant current mode and constant current output region (A). Further, as is illustrated in FIG. 9, the duty cycle comparison signals may also result in the electrosurgical generator operating in the region $P_1$ of the constant power output region (B), or the region $P_2$ of the constant power output region (B). Therefore, in one exemplary embodiment, mode selector 513 is configured to determine the operating mode basd at least in part on comparisons of the buck converter duty cycle $d_{buck}$ and boost inverter duty cycle $d_{boost}$ to the duty cycle limits and to generate mode output signals to control steering logic 514 and/or current mode controller 511.

In accordance with an exemplary embodiment, both the current-mode control 311 and the current-mode controller 511 may be able to maintain an approximately constant value of inductor current $i_L(t)$ by adjusting the current within 1-2 cycles. In another exemplary embodiment, the current-mode controller adjusts the inductor current within 1-10 cycles. In yet another embodiment, the current-mode controller adjusts the inductor within 10-100 cycles. Any of these examples may comprise a "low cycle" adjustemtn. This low cycle adjustment can be considered "deadbeat control" or "near-deadbeat control". In accordance with an exemplary embodiment, near-deadbeat control minimizes unintentional charring by ensuring that only the requested quantum of power is delivered to the electrosurgical instrument. In the prior art, slow transient response of the converter to changes in load impedance may result in excessive delivery of power that may not be detected for 500 cycles or more. Stated another way, in an exemplary embodiment, an electrosurgical generator has an operating bandwidth of 100-500 kHz, compared to the prior art bandwidth of 1-10 kHz.

Figure 10:
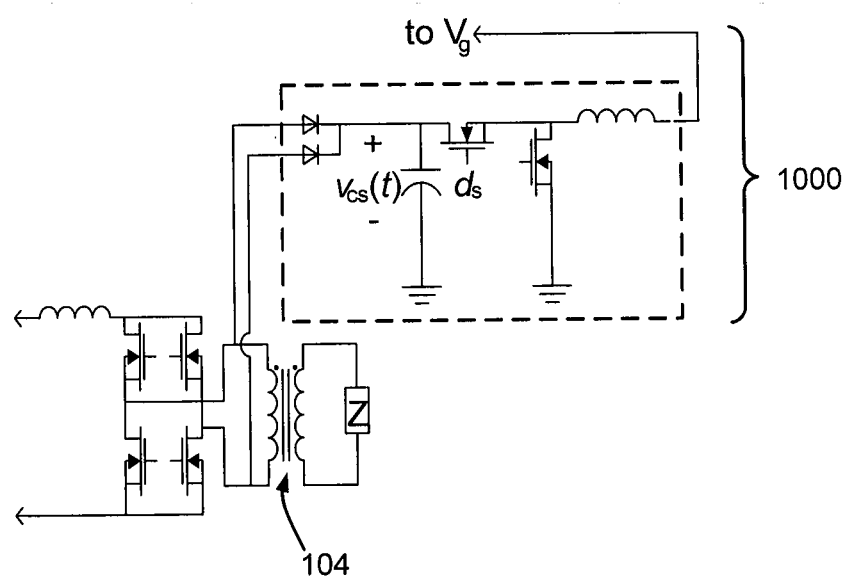
FIG. 10 illustrates a schematic of an exemplary non-dissipative snubber circuit, in accordance with various embodiments.

Although the mode transitions operate with near-deadbeat control, it still takes at least 1-2 cycles to change modes, and in some embodiments up to 100 cycles. Thus, should the load impedance suddenly increase while in either constant power mode, the converter will continue to supply constant power for the remainder of at least one cycle before transitioning to the constant voltage mode. In accordance with an exemplary embodiment and with reference to FIG. 10, an electrosurgical generator further comprises a non-dissipative voltage snubber circuit 1000 to prevent undesirable voltage spikes. The snubber circuit 1000 may be coupled to an electrosurgical generator such as electrosurgical generator 300 or electrosurgical generator 500. The non-dissipative voltage snubber circuit 1000 is coupled to the primary winding of the transformer 104. In an exemplary embodiment, a duty cycle $d_S$ of snubber circuit 1000 is varied to maintain $v_{CS}(t)$ at a fixed value. Furthermore, instruments used for electrosurgery typically have leads that are several meters long. The long leads can result in an inductive load to the electrosurgical generator. Therefore, snubber circuit 1000 may further be configured to damp voltage spikes generated when switching the inductive load.

In general, any number of current, voltage, or duty cycle limits, and any number of subdivisions of constant current, constant power, or constant voltage modes may be used to facilitate operating mode selection and transition in order to provide near deadbeat control of an electrosurgical generator. The electrosurgical generator may include any electrosurgical generator control system comprising a mode selector that determines the current operating mode, steering logic that selects from the possible operating modes of constant current, constant power, or constant voltage, where the operating mode is based in part on the outputs of a current mode controller and a voltage mode controller. The operating mode and transitions between operating mode are configured to provide near deadbeat control of an electrosurgical generator having both a DC-DC buck converter and a DC-AC boost inverter.

Failure to maintain either accurate regulation of output power or sufficient means of voltage limiting may lead to higher output voltages, leading to unintentional charring, or higher output power, leading to unintentional thermal spread. The exemplary embodiments of the electrosurgical generators described herein accurately and quickly maintain the proper power characteristics, and allow a user to control the cutting process.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as critical, required, or essential features or elements of any or all the draft statements. As used herein, the terms "includes," "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Further, no element described herein is required for the practice of the invention unless expressly described as "essential" or "critical."

The invention claimed is:

1. An electrosurgical generator (ESG) controller of an electrosurgical generator, wherein the ESG controller comprises:
   a current-mode controller configured to compare an inductor current $i_L(t)$ to a control current limit $i_C$, and wherein the current-mode controller is configured generate a current-mode controller signal for use during either a constant current operating mode of the ESG or a constant power operating mode of the ESG;
   a voltage-mode controller configured to compare an output voltage $v_{out}(t)$ with a reference voltage $V_{max}$, and wherein the voltage-mode controller is configured to generate a voltage-mode controller signal for use during a constant voltage operating mode of the electrosurgical generator;
   a mode selector configured to compare the inductor current $i_L(t)$ and the output voltage $v_{out}(t)$ to respective current limits and voltage limits and to generate an operating mode indicator; and
   steering logic configured to receive: the operating mode indicator, and steering logic input signals; wherein the steering logic input signals comprise: the current-mode controller signal having a first duty cycle $d_1(t)$, the voltage-mode controller signal having a second duty cycle $d_2(t)$, a third signal having a fixed duty cycle $d_3$, and a fourth signal having a fixed duty cycle $d_4$;

wherein the steering logic is configured to provide a first driver signal to the electrosurgical generator at a first controller output and a second driver signal to the electrosurgical generator at a second controller output;

wherein the steering logic is further configured to select an operating mode of the ESG from one of the constant current operating mode of the ESG, the constant power operating mode of the ESG, or the constant voltage operating mode of the ESG based on the operating mode indicator and by providing the first driver signal and the second driver signal, wherein the first driver signal and the second driver signal are provided to the electrosurgical generator based on the operating mode indicator, for providing near dead-beat control of the ESG.

2. The ESG controller of claim 1, wherein the current-mode controller is configured to compare $i_L(t)$ to the control current limit $i_C$, that is set by a user or provided by a look-up table, and to adjust the first duty cycle of the current-mode controller signal to maintain a constant $i_L(t)$.

3. The ESG controller of claim 1, wherein the comparison of the inductor current $i_L(t)$ to the control current limit $i_C$ is used to adjust the current-mode controller signal to cause the inductor current $i_L(t)$ to match the control current limit $i_C$.

4. The ESG controller of claim 1, wherein the voltage-mode controller comprises a comparator, a compensator, and a pulse-width modulator (PWM), wherein the voltage-mode controller compares the output voltage $v_{out}(t)$ with the reference voltage $V_{max}$ at the comparator, and wherein an output of the comparator is communicated to the compensator, and wherein the compensator outputs an error signal that drives the PWM, and wherein the PWM generates the second driver signal.

5. The ESG controller of claim 1, wherein, based on the operating mode indicator, the steering logic is further configured to selectively pass one of the steering logic input signals to the first driver signal, and another of steering logic input signals to the second driver signal, thereby selecting the operating mode of the ESG from one of the constant current operating mode of the ESG, the constant power operating mode of the ESG, or the constant voltage operating mode of the ESG.

6. The ESG controller of claim 5, wherein the fixed duty cycle $d_3$ is equal to zero and the fixed duty cycle $d_4$ is equal to one.

7. The ESG controller of claim 5, wherein the steering logic is configured:

to provide the first driver signal based on the current-mode controller signal and to provide the second driver signal based on the fourth signal, during the constant current operating mode of the ESG;

to provide the first driver signal based on the third signal and to provide the second driver signal based on the current-mode controller signal during the constant power operating mode; and to provide the first driver signal based on the third signal and to provide the second driver signal based on the voltage-mode controller signal during the constant voltage operating mode.

8. The ESG controller of claim 5, wherein the steering logic is configured:

to provide the first driver signal based on the current-mode controller signal and to provide the second driver signal based on the fourth signal, during the constant current operating mode of the ESG;

to provide the first driver signal based on the current-mode controller signal and to provide the second driver signal based on the fourth signal, during a first constant power operating mode of the ESG;

to provide the first driver signal based on the third signal and to provide the second driver signal based on the current-mode controller signal during a second constant power operating mode; and to provide the first driver signal based on the third signal and to provide the second driver signal based on the voltage-mode controller signal during the constant voltage operating mode;

wherein the current-mode controller signal is based on a comparison of $i_L(t)$ to (K*Pset) during the constant current operating mode and based on a comparison of $i_L(t)$ to a nonlinear time dependent variable during the first constant power operating mode.

9. An electrosurgical generator (ESG) controller of an electrosurgical generator, wherein the ESG controller comprises:

a current-mode controller configured to compare an inductor current $i_L(t)$ to a control current limit $i_C$, and wherein the current-mode controller is configured generate a current-mode controller signal for use during either a constant current operating mode of the ESG or a constant power operating mode of the ESG;

a voltage-mode controller configured to compare an output voltage $v_{out}(t)$ with a reference voltage Vmax, and wherein the voltage-mode controller is configured to generate a voltage-mode controller signal for use during a constant voltage operating mode of the electrosurgical generator;

a mode selector configured to compare the inductor current $i_L(t)$ and the output voltage $v_{out}(t)$ to respective current limits and voltage limits and to generate an operating mode indicator; and steering logic configured to receive: the operating mode indicator, and steering logic input signals; the steering logic input signals comprising: the current-mode controller signal having a first duty cycle $d_1(t)$, the voltage-mode controller signal having a second duty cycle $d_2(t)$, a third signal having a fixed duty cycle $d_3$, and a fourth signal having a fixed duty cycle $d_4$;

wherein, based on the operating mode indicator, the steering logic is configured to provide a first driver signal to the electrosurgical generator at a first controller output and a second driver signal to the electrosurgical generator at a second controller output, and to select an operating mode of the ESG from one of the constant current operating mode of the ESG, the constant power operating mode of the ESG, or the constant voltage operating mode of the ESG, for providing near dead-beat control of the ESG.

10. The ESG controller of claim 9, wherein the ESG controller can change the operating mode of the ESG within 1-100 cycles.

11. The ESG controller of claim 9, wherein the voltage-mode controller comprises a comparator, a compensator, and a pulse-width modulator (PWM), wherein the voltage-mode controller compares the output voltage $v_{out}(t)$ with the reference voltage $V_{max}$ at the comparator, and wherein an output of the comparator is communicated to the compensator, and wherein the compensator outputs an error signal that drives the PWM, and wherein the PWM generates the second driver signal.

12. The ESG controller of claim 9, wherein, based on the operating mode indicator, the steering logic is further configured to selectively pass one of the steering logic input signals to the first driver signal, and another of steering logic input signals to the second driver signal, thereby selecting the operating mode of the ESG from one of the constant current operating mode of the ESG, the constant power operating mode of the ESG, or the constant voltage operating mode of the ESG.

13. The ESG controller of claim 12, wherein the steering logic is configured:
   to pass the current-mode controller signal to the first controller output and the fourth signal to the second controller output, during the constant current operating mode of the ESG;
   to pass the third signal to the first controller output and the current-mode controller signal to the second controller output, during the constant power operating mode of the ESG; and
   to pass the third signal to the first controller output and the voltage-mode controller signal to the second controller output, during the constant voltage operating mode of the ESG.

14. The ESG controller of claim 12, wherein the steering logic is configured:
   to pass the current-mode controller signal to the first controller output and the fourth signal to the second controller output, during the constant current operating mode of the ESG;
   to pass the current-mode controller signal to the first controller output and the fourth signal to the second controller output, during a first constant power operating mode of the ESG;
   to pass the third signal to the first controller output and the current-mode controller signal to the second controller output, during a second constant power operating mode of the ESG; and
   to pass the third signal to the first controller output and the voltage-mode controller signal to the second controller output, during the constant voltage operating mode of the ESG;
   wherein the current-mode controller signal is based on a comparison of $i_L(t)$ to (K*Pset) during the constant current operating mode and based on a comparison of $i_L(t)$ to a nonlinear time dependent variable during the first constant power operating mode.

15. An electrosurgical generator (ESG) controller of an electrosurgical generator, wherein the ESG controller comprises:
   a current-mode controller configured to compare an inductor current $i_L(t)$ to a control current limit $i_C$, and wherein the current-mode controller is configured generate a current-mode controller signal for use during either a constant current operating mode of the ESG or a constant power operating mode of the ESG;
   a voltage-mode controller configured to compare an output voltage $v_{out}(t)$ with a reference voltage $V_{max}$, and wherein the voltage-mode controller is configured to generate a voltage-mode controller signal for use during a constant voltage operating mode of the electrosurgical generator;
   a mode selector configured to compare the inductor current $i_L(t)$ and the output voltage $v_{out}(t)$ to respective current limits and voltage limits and to generate an operating mode indicator; and
   steering logic configured to receive: the operating mode indicator, and steering logic input signals; wherein the steering logic input signals comprise: the current-mode controller signal having a first duty cycle $d_1(t)$, the voltage-mode controller signal having a second duty cycle $d_2(t)$, a third signal having a fixed duty cycle $d_3$, and a fourth signal having a fixed duty cycle $d_4$;
   wherein the steering logic is configured to provide a first driver signal to the electrosurgical generator at a first controller output and a second driver signal to the electrosurgical generator at a second controller output;
   wherein, based on the operating mode indicator, the steering logic is further configured to selectively pass one of the steering logic input signals to the first driver signal, and another of steering logic input signals to the second driver signal, thereby selecting an operating mode of the ESG from one of the constant current operating mode of the ESG, the constant power operating mode of the ESG, or the constant voltage operating mode of the ESG, for providing near dead-beat control of the ESG.

16. The ESG controller of claim 15, wherein the comparison of the inductor current $i_L(t)$ to the control current limit $i_C$ is used to adjust the current-mode controller signal to cause the inductor current $i_L(t)$ to match the control current limit $i_C$.

17. The ESG controller of claim 15, wherein the voltage-mode controller comprises a comparator, a compensator, and a pulse-width modulator (PWM), wherein the voltage-mode controller compares the output voltage $v_{out}(t)$ with the reference voltage $V_{max}$ at the comparator, and wherein an output of the comparator is communicated to the compensator, and wherein the compensator outputs an error signal that drives the PWM, and wherein the PWM generates the second driver signal.

18. The ESG controller of claim 15, wherein the fixed duty cycle $d_3$ is equal to zero and the fixed duty cycle $d_4$ is equal to one.

19. The ESG controller of claim 15, wherein the steering logic is configured:
   to provide the first driver signal based on the current-mode controller signal and to provide the second driver signal based on the fourth signal, during the constant current operating mode of the ESG;
   to provide the first driver signal based on the third signal and to provide the second driver signal based on the current-mode controller signal during the constant power operating mode; and
   to provide the first driver signal based on the third signal and to provide the second driver signal based on the voltage-mode controller signal during the constant voltage operating mode.

20. The ESG controller of claim 15, wherein the steering logic is configured:
   to provide the first driver signal based on the current-mode controller signal and to provide the second driver signal based on the fourth signal, during the constant current operating mode of the ESG;
   to provide the first driver signal based on the current-mode controller signal and to provide the second driver signal based on the fourth signal, during a first constant power operating mode of the ESG;
   to provide the first driver signal based on the third signal and to provide the second driver signal based on the current-mode controller signal during a second constant power operating mode; and
   to provide the first driver signal based on the third signal and to provide the second driver signal based on the voltage-mode controller signal during the constant voltage operating mode;

wherein the current-mode controller signal is based on a comparison of $i_L(t)$ to (K*Pset) during the constant current operating mode and based on a comparison of $i_L(t)$ to a nonlinear time dependent variable during the first constant power operating mode.

* * * * *